United States Patent
Hosaka et al.

(10) Patent No.: US 10,058,286 B2
(45) Date of Patent: Aug. 28, 2018

(54) BIOLOGICAL INFORMATION MONITORING APPARATUS

(71) Applicant: NIHON KOHDEN CORPORATION, Tokyo (JP)

(72) Inventors: Shoichi Hosaka, Tokyo (JP); Toshiki Aoki, Tokyo (JP); Shogo Maeda, Tokyo (JP); Osamu Uchida, Osaka (JP)

(73) Assignee: NIHON KOHDEN CORPORATION, Tokyo (JP)

( * ) Notice: Subject to any disclaimer, the term of this patent is extended or adjusted under 35 U.S.C. 154(b) by 686 days.

(21) Appl. No.: 13/862,974

(22) Filed: Apr. 15, 2013

(65) Prior Publication Data

US 2013/0274617 A1    Oct. 17, 2013

(30) Foreign Application Priority Data

Apr. 16, 2012 (JP) .................. 2012-092790

(51) Int. Cl.
*A61B 5/00* (2006.01)
*G01N 33/48* (2006.01)
(Continued)

(52) U.S. Cl.
CPC ............... *A61B 5/72* (2013.01); *A61B 5/082* (2013.01); *A61B 5/1495* (2013.01); *A61B 5/742* (2013.01);
(Continued)

(58) Field of Classification Search
CPC ........... A61B 5/00; A61B 5/0004; A61B 5/02; A61B 5/024; A61B 5/0402; A61B 5/082; A61B 5/72; A61B 5/1495; G06F 19/00
See application file for complete search history.

(56) References Cited

U.S. PATENT DOCUMENTS

| 5,899,855 A | 5/1999 | Brown |
| 6,280,382 B1 | 8/2001 | Rautava |

(Continued)

FOREIGN PATENT DOCUMENTS

| CN | 101176663 B | 10/2010 |
| JP | 9-133646 A | 5/1997 |

(Continued)

OTHER PUBLICATIONS

European Search Report for EP Patent App. No. 13163712.6 (dated Jul. 20, 2013).

(Continued)

*Primary Examiner* — Jacqueline Cheng
*Assistant Examiner* — Jairo Portillo
(74) *Attorney, Agent, or Firm* — Pearne & Gordon LLP

(57) ABSTRACT

A biological information monitoring apparatus includes: a measurer which is configured to measure biological information of a subject; a display on which a measurement value of the biological information measured by the measurer is displayed; a calibration controller which, when a predetermined condition is satisfied, is configured to perform a calibration process on the measurer; a time measurer which is configured to acquire a remaining time before the calibration process is ended; and a display controller which is configured to cause an index indicating the remaining time to be displayed on the display.

5 Claims, 6 Drawing Sheets

(51) Int. Cl.
    *A61B 5/1495*     (2006.01)
    *A61B 5/08*     (2006.01)
    *G16H 40/40*     (2018.01)
    *A61B 10/00*     (2006.01)
    *A61B 5/091*     (2006.01)

(52) U.S. Cl.
    CPC .............. *G01N 33/48* (2013.01); *G16H 40/40* (2018.01); *A61B 5/091* (2013.01); *A61B 2010/0087* (2013.01); *A61B 2505/05* (2013.01)

(56) References Cited

U.S. PATENT DOCUMENTS

| | | | |
|---|---|---|---|
| 6,711,425 B1* | 3/2004 | Reuss | A61B 5/14542 600/323 |
| 2003/0135087 A1 | 7/2003 | Hickle et al. | |
| 2004/0147847 A1 | 7/2004 | Ng et al. | |
| 2005/0101907 A1* | 5/2005 | Sondeen | A61M 5/1723 604/28 |
| 2005/0222514 A1 | 10/2005 | Sugo et al. | |
| 2005/0273016 A1* | 12/2005 | Colman | A61B 5/083 600/529 |
| 2007/0034792 A1 | 2/2007 | Zhang et al. | |
| 2007/0107728 A1* | 5/2007 | Ricciardelli | A61B 5/087 128/204.21 |
| 2007/0265514 A1* | 11/2007 | Kiani | A61B 5/14542 600/365 |
| 2008/0098795 A1 | 5/2008 | Orr | |
| 2008/0300572 A1* | 12/2008 | Rankers | A61B 5/14532 604/504 |
| 2009/0018426 A1* | 1/2009 | Markle | A61B 5/14532 600/365 |
| 2009/0326335 A1 | 12/2009 | Baker et al. | |
| 2010/0268101 A1 | 10/2010 | Sugo | |
| 2011/0140912 A1 | 6/2011 | Gross et al. | |
| 2011/0196211 A1* | 8/2011 | Al-Ali | A61B 5/14551 600/300 |
| 2011/0314896 A1* | 12/2011 | Carlson | A61B 5/411 73/23.3 |
| 2012/0262298 A1* | 10/2012 | Bohm | G01N 27/3274 340/604 |

FOREIGN PATENT DOCUMENTS

| | | |
|---|---|---|
| JP | 2000-245711 A | 9/2000 |
| JP | 2005-348975 A | 12/2005 |
| JP | 2006-516446 A | 7/2006 |
| JP | 2010-508523 A | 3/2010 |
| JP | 2010-148964 A | 7/2010 |
| JP | 2010-246801 A | 11/2010 |
| JP | 4742644 B2 | 8/2011 |
| JP | 2012-500699 A | 1/2012 |
| WO | WO2011/026053 A1 | 3/2011 |

OTHER PUBLICATIONS

Japanese Office Action for the related Japanese Patent Application No. 2012-092790 dated Sep. 29, 2015.

Office Action issued in Patent Application No. EP 13 163 712.6 dated Feb. 22, 2017.

* cited by examiner

BIOLOGICAL INFORMATION MONITORING APPARATUS

CROSS-REFERENCE TO RELATED APPLICATION(S)

This application is based upon and claims the benefit of priority from prior Japanese patent application No. 2012-092790, filed on Apr. 16, 2012, the entire contents of which are incorporated herein by reference.

BACKGROUND

The presently disclosed subject matter relates to a biological information monitoring apparatus which measures biological information of the subject, and which includes a display that displays the measurement value of the biological information.

As an apparatus of this kind is an apparatus in which the concentration of a predetermined gas (carbon dioxide, oxygen, a volatile anesthetic agent, or the like) contained in the expired gas of the subject is measured as biological information by a sensor, and the measurement value is displayed on a display (for example, see JP-T-2010-508523 and JP-A-2000-245711).

In a sensor, the measurement accuracy may be sometimes lowered over time by various causes, and therefore calibration must be performed at an adequate timing. In an apparatus of this kind, when a given requirement is satisfied (for example, in activation of the apparatus, or elapse of a prescribed time period from a previous calibration process), the operation mode is automatically shifted to a mode in which a calibration process is performed. During a period when a calibration process is performed, biological information cannot be measured, and therefore the portion in which the biological information is to be displayed is set to a state where a measurement value is not displayed (for example, "- - -" is displayed) (hereinafter, the state is referred to as the measurement value non-displayed state).

From the standpoint of the observer monitoring biological information, it is often that the shifting to the calibration mode cannot be expected. Furthermore, the time period required for calibration is different in each case. Therefore, waiting for the end of the calibration process in which the end of the process is not known, and which is performed in the state measurement value non-displayed state causes the observer to have serious stress. In the case where such a monitoring apparatus is used for monitoring the condition of the patient under surgery, moreover, waiting for the end of the calibration process causes the working efficiency of the surgery personnel to be lowered.

SUMMARY

The presently disclosed subject matter may provide a biological information monitoring apparatus which can relieve the stress that, during shifting to the calibration mode, is applied to the observer monitoring biological information, and avoid lowering of the working efficiency.

The biological information monitoring apparatus may comprise: a measurer which is configured to measure biological information of a subject; a display on which a measurement value of the biological information measured by the measurer is displayed; a calibration controller which, when a predetermined condition is satisfied, is configured to perform a calibration process on the measurer; a time measurer which is configured to acquire a remaining time before the calibration process is ended; and a display controller which is configured to cause an index indicating the remaining time to be displayed on the display.

The index may be at least one of a numeral and a progress bar.

Based on the predetermined condition, the time measurer may select one of a plurality of predetermined values which indicate times required for the calibration process, respectively, and, based on the selected one of the plurality of predetermined values, acquire the remaining time.

Based on information indicating a relationship between the predetermined condition and a time required for the calibration process, the time measurer may calculate or acquire the remaining time.

The biological information may include at least one of a concentration of a predetermined gas contained in an expired gas of the subject, a concentration of an anesthetic agent contained in an expired gas of the subject, a respiratory volume, and an airway pressure.

The biological information may include at least two or more of an electrocardiogram, a pulse wave, and a blood pressure, and the measurer may include a calculator which is configured to calculate a cardiac output of the subject, based on the at least two or more biological information.

The predetermined condition may relate to at least one of an elapsed time from a previous calibration process, an elapsed time from activation of the biological information monitoring apparatus, a current time, a temperature in the biological information monitoring apparatus, an atmospheric pressure, an input of an instruction by an operator, and stabilization of a signal relating to the biological information.

DETAILED DESCRIPTION OF EXEMPLARY EMBODIMENTS

Hereinafter, embodiments of the presently disclosed subject matter will be described in detail with reference to the accompanying drawings.

Figure 1:
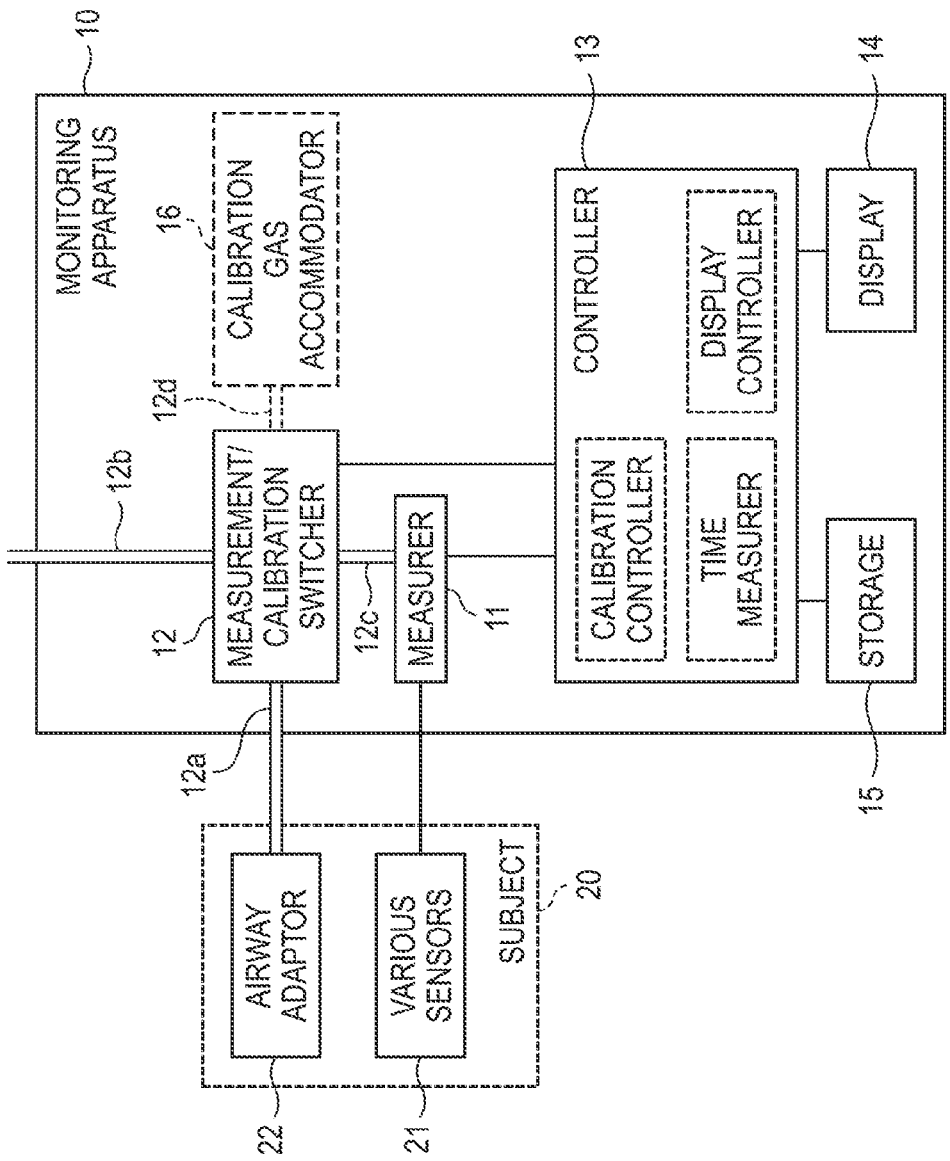
FIG. 1 is a functional block diagram showing the configuration of a monitoring apparatus of a first embodiment of the presently disclosed subject matter.

FIG. 1 is a functional block diagram showing the configuration of a biological information monitoring apparatus (hereinafter, referred to simply as the monitoring apparatus) of a first embodiment of the presently disclosed subject matter. The monitoring apparatus 10 includes a measurer 11, a measurement/calibration switcher 12, a controller 13, a display 14, and a storage 15.

A plurality of kinds of signals relating to biological information which is acquired through various sensors 21 (including electrodes, a cuff, and the like) attached to the subject 20 are supplied to the measurer 11 directly or through a network. Examples of biological information of the subject are the pulse rate, an electrocardiogram, the blood pressure, the oxygen saturation, etc. The measurer 11 obtains measurement values of various kinds of biological information based on the supplied signals.

The measurement/calibration switcher 12 includes a related-art valve device (not shown) which selectively causes one of a respiratory gas introducing passage 12a and an atmosphere opening passage 12b to communicate with a measurement gas passage 12c. The respiratory gas introducing passage 12a is connected an airway adaptor 22 which is attached to the mouth or nose of the subject 20. One end of the atmosphere opening passage 12b is opened in the atmosphere.

The valve device of the measurement/calibration switcher 12 normally causes the respiratory gas introducing passage 12a to communicate with the measurement gas passage 12c. The respiratory gas of the subject 20 is introduced into the measurer 11 through the respiratory gas introducing passage 12a and the measurement gas passage 12c.

The measurer 11 includes various related-art gas sensors (not shown), and is configured so as to measure the concentrations of specific gasses contained in the respiratory gas of the subject. In the embodiment, the measurer 11 acquires measurement values of the concentrations of specific gasses, i.e., carbon dioxide ($CO_2$), oxygen ($O_2$), laughing gas ($N_2O$), and isoflurane (ISO) which is a volatile anesthetic agent.

The controller 13 is communicably connected to the measurer 11, and receives measurements values which are acquired by the measurer 11 based on the inputs from the various sensors 21, and measurement values of the concentrations of the various gasses which are acquired from the respiratory gas of the subject.

The display 14 is a displaying device which is disposed in the front surface of the apparatus, and communicably connected to the controller 13. The controller 13 causes the various measurement values which are received through the measurer 11, to be displayed in real time on the display 14.

Figure 2:
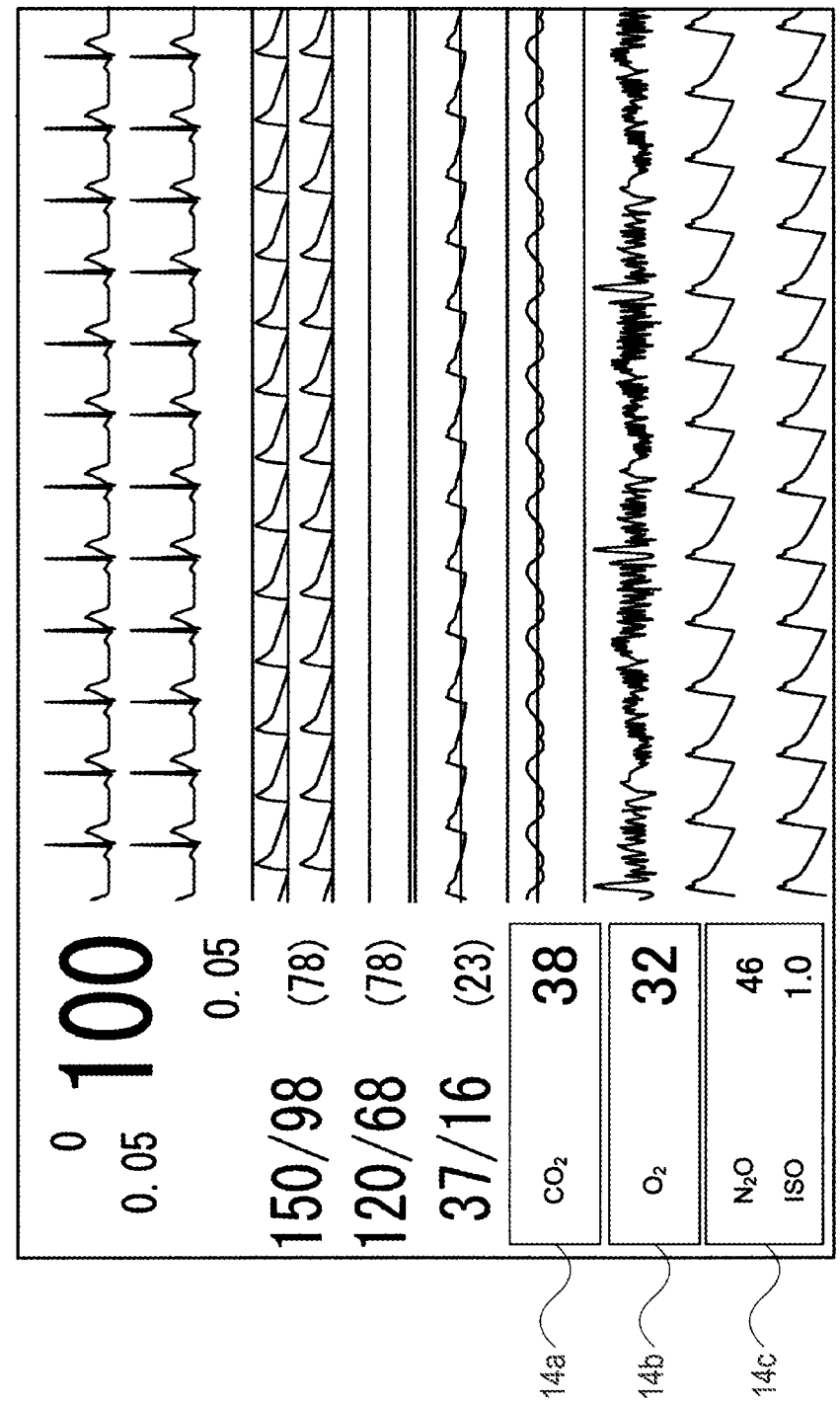
FIG. 2 is a view showing an example of a screen displayed on a display of the monitoring apparatus of FIG. 1.

FIG. 2 is a view showing an example of a screen displayed on the display 14. Based on the measurement values which are supplied from the measurer 11 to the controller 13, the various kinds of biological information are displayed in the form of a waveform or numerals. In the lower left portion of the screen, an area for displaying the measurement values of the concentrations of carbon dioxide, oxygen, laughing gas, and isoflurane which are contained in the expired gas of the subject 20 is disposed. Specifically, the measurement value of the concentration of carbon dioxide is displayed in a first concentration display region 14a, that of oxygen is displayed in a second concentration display region 14b, and the measurement values of the concentrations of laughing gas and isoflurane are displayed in a third concentration display region 14c.

The accuracies of the gas sensors provided in the measurer are varied over time or depending on the surrounding environment. In order to supply correct measurement values to the controller 13, it is necessary to calibrate the gas sensors at an adequate timing. The controller 13 functions as the calibration controller in the presently disclosed subject matter, and is configured so that, when predetermined conditions are satisfied, it is automatically shifted to a calibration mode, and performs a calibration process on the gas sensors.

Specifically, the calibration process for the gas sensors is performed immediately after activation of the monitoring apparatus 10, and at a timing when the elapsed time from the previous calibration process exceeds a predetermined value. In this case, the controller 13 functions as a time measurer to perform time measurement, and it is determined that the elapsed time from the previous calibration reaches the predetermined value.

As shown in FIG. 1, the controller 13 is communicably connected to the measurement/calibration switcher 12. When the predetermined conditions are satisfied, the controller 13 controls the valve device of the measurement/calibration switcher 12 so as to cause the atmosphere opening passage 12b to communicate with the measurement gas passage 12c. As a result, the atmosphere is introduced into the measurer 11 through the atmosphere opening passage 12b and the measurement gas passage 12c, and the gas sensors are calibrated based on the composition of the atmosphere. The calibration process is well known, and therefore its detailed description is omitted.

Figure 3:
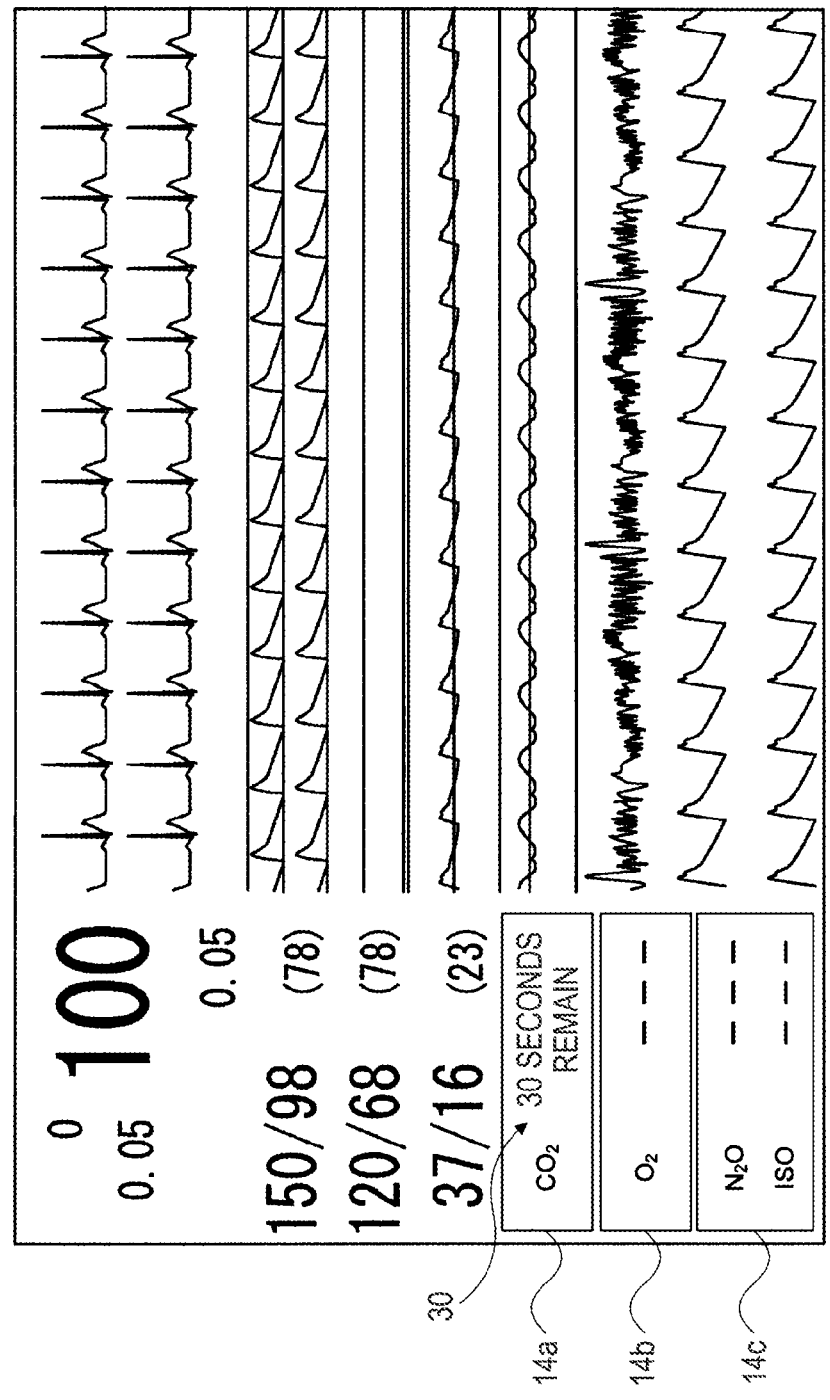
FIG. 3 is a view showing another example of the screen displayed on the display of the monitoring apparatus of FIG. 1.

During execution of the calibration process, the respiratory gas of the subject 20 is not introduced into the measurer 11 through the respiratory gas introducing passage 12a. Therefore, the measurer 11 cannot acquire measurement values of the concentrations of the specific gasses contained in the expired gas of the subject 20. In this case, as shown in FIG. 3, the second concentration display region 14b and the third concentration display region 14c are set to the measurement value non-displayed state where "- - -" is displayed.

By contrast, the controller 13 which functions as the time measurer acquires the remaining time before the calibration process for the gas sensors is ended. In the case where the calibration process which is to be performed after activation of the apparatus requires 60 seconds, and those which are to be periodically executed after each elapse of a predetermined time (for example, each elapse of 1 hour after activation) require 20 second, for example, two predetermined values which indicate the required times for the calibration process, respectively, i.e., 60 seconds and 20 seconds are stored in the storage 15. In accordance with the conditions which are satisfied at the timing when the calibration process is to be performed, the controller 13 selects one of the predetermined values, and reads out it.

The controller 13 which functions as the time measurer starts the time measuring process for the predetermined value that is readout from the storage 15. In the calibration process which is performed immediately after activation of the apparatus, for example, the process of measuring the time or 60 seconds which is the predetermined value read out from the storage 15 is started. The remaining time before the calibration process is ended is acquired by direct subtraction of the read out predetermined value, or by subtracting the measured time from the read out predetermined value.

The controller 13 also functions as the display controller in the presently disclosed subject matter, and causes an index indicating the acquired remaining time to be displayed on the display 14. In the first concentration display region 14a, as shown in FIG. 3, a message which is an index, and which indicates the remaining time is displayed in place of the display of "- - -" showing the state where the measurement of the concentration of carbon dioxide is disabled. The example of FIG. 3 shows a state where 30 seconds have elapsed after starting of the calibration process which is performed after activation of the monitoring apparatus 10, and a message 30 of "30 seconds remain" is displayed in the first concentration display region 14a.

According to the configuration of the embodiment, the observer monitoring the biological information can view the remaining time before the calibration process is ended. Even when the shifting to the calibration mode is unexpected to the observer monitoring the biological information, therefore, the operator can know the remaining time, and hence stress during the waiting state can be largely relieved. When the remaining time which is known by the observer is allocated for another work, or like, the working efficiency of nursing care or surgery can be improved.

Based on predetermined conditions, the controller 13 functioning as the time measurer selects one of a plurality of predetermined values which indicate required times for the calibration process, respectively, from the storage 15, and, based on the selected predetermined value, acquires the remaining time. Therefore, it is possible to provide a display mode in which stress can be relieved while suppressing the calculation load of the controller 13.

The controller 13 is an arithmetic processing circuit which is configured by including an arithmetic device such as a CPU. The functions as the above-described calibration controller, time measurer, and display controller can be realized by the operation of hardware such as circuit devices, that of software such as programs stored in the arithmetic device, or a combination of these operations.

Figure 4:
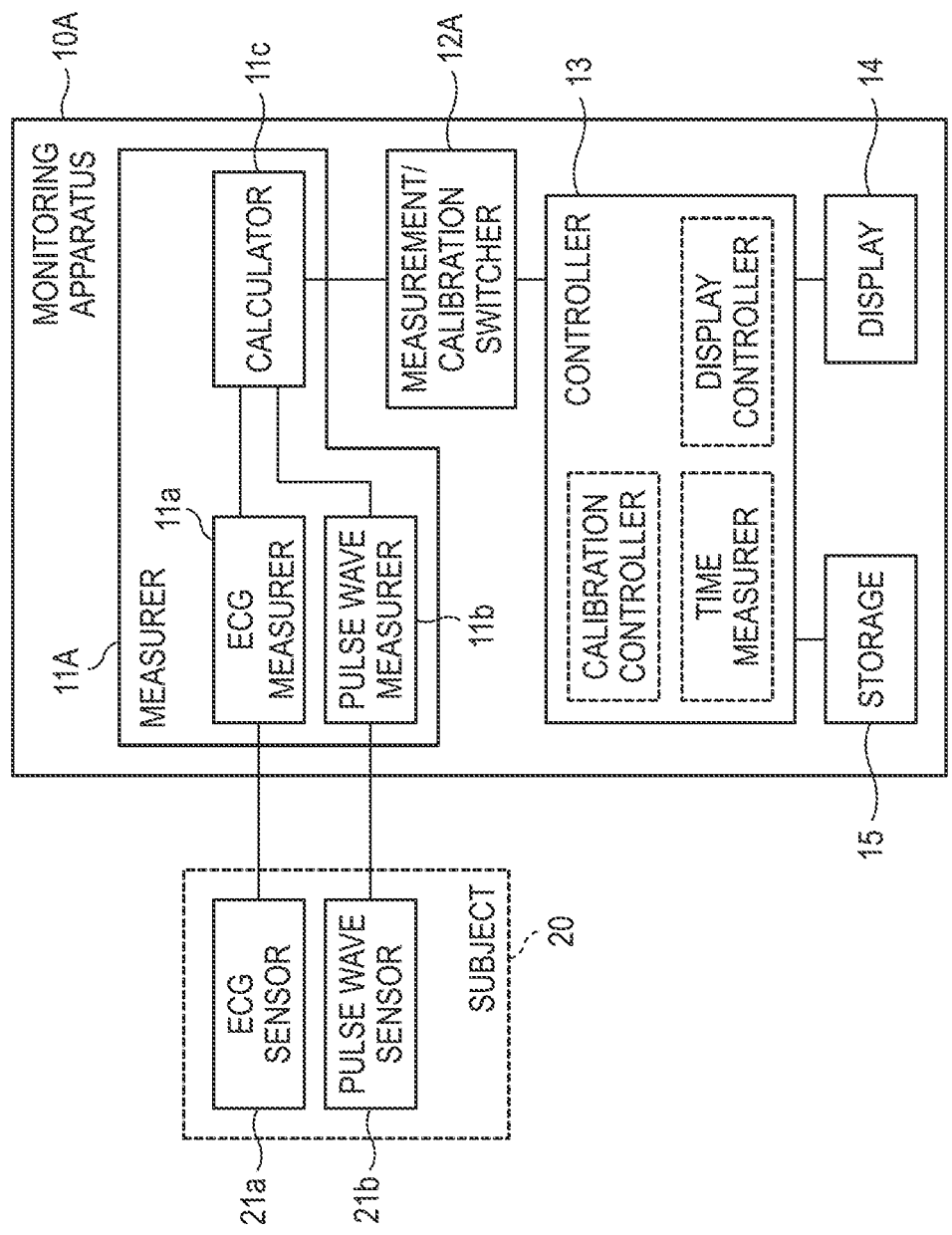
FIG. 4 is a functional block diagram showing the configuration of a monitoring apparatus of a second embodiment of the presently disclosed subject matter.

Next, a monitoring apparatus 10A of a second embodiment of the presently disclosed subject matter will be described with reference to FIG. 4. Components which are identical with or equivalent to those of the monitoring apparatus 10 of the first embodiment are denoted by the same reference numerals, and duplicated description is omitted.

The monitoring apparatus 10A of the embodiment includes a measurer 11A. The measurer 11A calculates the cardiac output based on an electrocardiogram (ECG) and pulse wave which are biological information measured from the subject 20.

Signals which relate to the electrocardiogram and the pulse wave, respectively, and which are acquired through an ECG sensor 21a and pulse wave sensor 21b that are attached to the subject 20 are supplied to an ECG measurer 11a and pulse wave measurer 11b in the measurer 11A. The measurer 11A further includes a calculator 11c. The calculator 11c obtains by calculation the cardiac output of the subject 20 by, for example, the technique disclosed in Japanese Patent No. 4,742,644. It is assumed that "measurement value" in the presently disclosed subject matter includes a value which is obtained by calculation based on biological information in this way.

In order to obtain the cardiac output, the calculator 11c requires information (for details, see JP-A-2010-246801) of the subject, and an ECG signal and pulse wave signal which are stably obtained for several minutes. Therefore, the calculation result (measurement value) of the cardiac output cannot be immediately sent to the controller 13, and hence a calibration process for several minutes is necessary for obtaining the average value of the cardiac output. When the controller 13 functions as the calibration controller, the calibration process is performed.

The calibration time depends also on the measurement environment, and therefore is hardly identified in an unambiguous manner. This causes the observer to have serious stress. In the embodiment, therefore, a measurement/calibration switcher 12A transmits either one of a calculation result (measurement value) of the cardiac output which is obtained as a result of calculation, and a signal indicating that the measurer 11A is performing a calculation process, to the controller 13 in accordance with the operation status of the calculator 11c.

Upon receiving the signal indicating that the measurer 11A is performing a calculation process, the controller 13 which functions as the time measurer in the presently disclosed subject matter acquires the remaining time before the calibration process performed by the measurer 11A is ended (i.e., the time elapsing before the state where the calculation result can display is attained) in a similar manner as the first embodiment. The controller 13 which functions as the display controller in the presently disclosed subject matter causes the index indicating the acquired remaining time to be displayed on the display 14 in a similar manner as the first embodiment.

The embodiments have been described in order to facilitate understanding of the presently disclosed subject matter, and are not intended to limit the presently disclosed subject matter. It is a matter of course that the presently disclosed subject matter may be changed or improved without departing the spirit thereof, and includes equivalents thereof.

The index which is displayed on the display 14 by the controller 13 functioning as the display controller, and which indicates the remaining time before the calibration process is ended is not limited to the above-described one, and may be displayed by using adequate characters, symbol, graph, chart, or the like from which the remaining time can be known.

Figure 5:
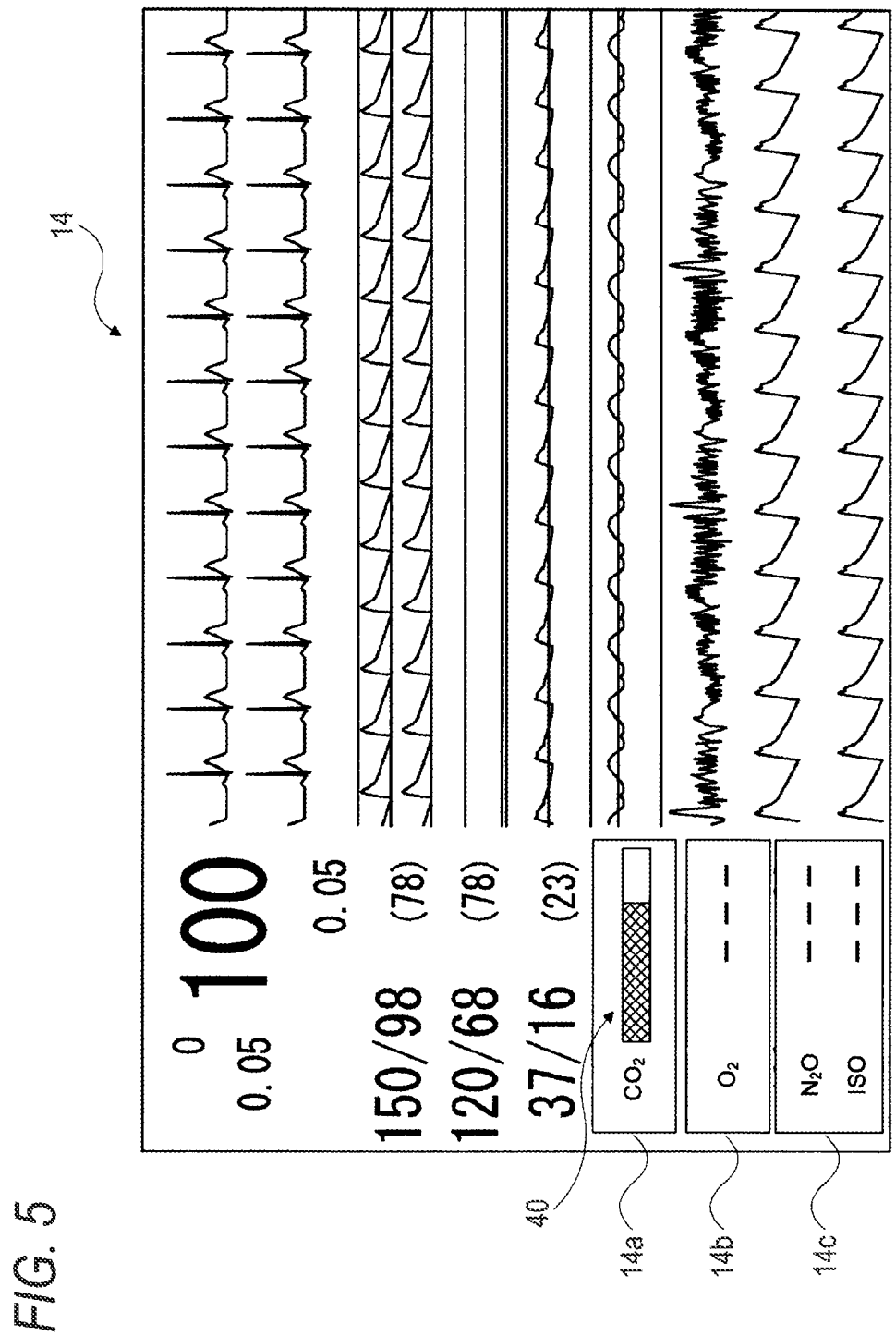
FIG. 5 is a view showing a further example of the screen displayed on the display of the monitoring apparatus of FIG. 1.

As shown in FIG. 5, for example, a progress bar 40 which visualizes the progress of the process may be used as the index. The controller 13 functioning as the time measurer obtains the rate of the elapsed time from the calibration process with respect to the predetermined value which is read out from the storage 15, and which indicates the required time for the calibration process, and the controller 13 functioning as the display controller changes the length of the progress bar 40 in accordance with the obtained rate. According to the configuration, the observer monitoring a biological signal can know the progress situation (the amount of the remaining time) of the calibration process by means of viewing, and stress during the waiting state can be relieved.

Figure 6:
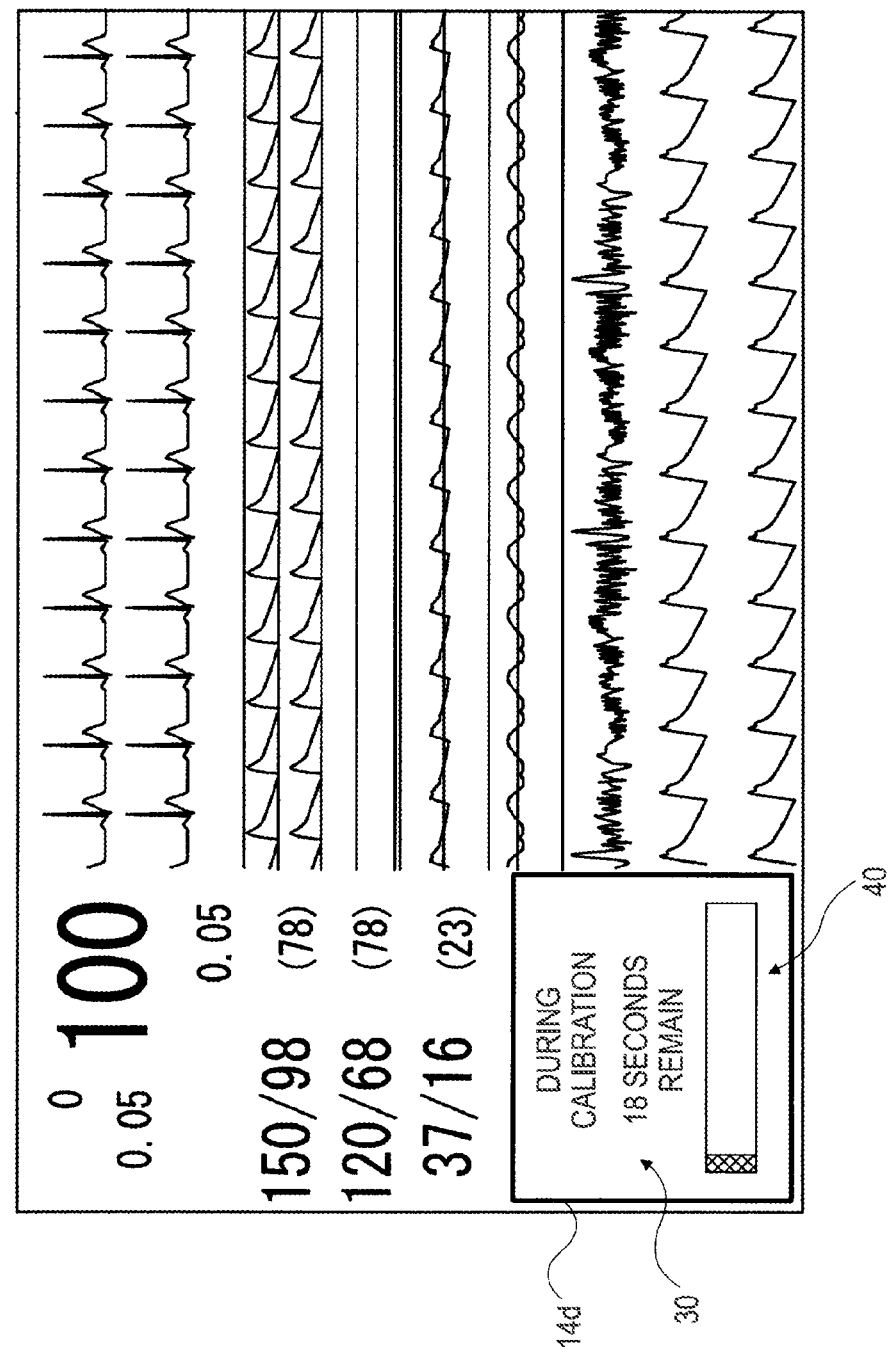
FIG. 6 is a view showing a still further example of the screen displayed on the display of the monitoring apparatus of FIG. 1.

As shown in FIG. 6, both the message 30 including numerals and the progress bar 40 may be used as the index. In this example, a dedicated display region 14d for displaying the index indicating the remaining time before the calibration process is ended is displayed in place of the first to third concentration display regions 14a to 14c where the measurement non-displayed state is set. In the figure, the state where 2 seconds have elapsed after the measurement of 20 seconds read out as the predetermined value from the storage 15 is started as a result that the elapsed time from the previous calibration reaches the predetermined value is exemplarily shown.

In place of or in addition to the configuration where the predetermined value indicating the required calibration time is previously stored in the storage 15, a configuration may be employed where the storage 15 stores information indicating relationships between the predetermined conditions and the required calibration time in the form of a table or a function, and the controller 13 functioning as the time measurer calculates or acquires the remaining time before the calibration process is ended, based on the information.

In place of or in addition to the conditions where the monitoring apparatus 10 has been activated, and where the elapsed time from the previous calibration process reaches the predetermined value, conditions such as the elapsed time from activation of the monitoring apparatus 10, the current time, the temperature in the apparatus, the atmospheric pressure, an input of an instruction for executing the calibration process by the operator, and stabilization of a signal relating to the biological information may set as the predetermined conditions. According to the configuration, even in a situation where the required time is different depending on the predetermined conditions, the remaining time can be correctly acquired.

With respect to the elapsed time and the current time, the time measurer provided in the controller 13, an internal timer (not shown), or the like is used, and, with respect to the temperature in the apparatus and the atmospheric pressure, sensors which can measure these parameters are disposed, whereby it is enabled to determine whether the predetermined conditions are satisfied or not.

The biological information which relates to the respiration of the subject 20, and which is measured by the measurer 11 of the monitoring apparatus 10 of the first embodiment is not limited to the above-described concentrations of carbon dioxide, oxygen, laughing gas, and isoflurane. Another example of the volatile anesthetic agent which is to be measured is at least one of enflurane, sevoflurane, halothane, and desfluran. Alternatively, a configuration where the respiratory volume and the airway pressure are measured as biological information may be employed.

A configuration where, as indicated by the broken line in FIG. 1, a calibration gas passage 12d connected to a calibration gas accommodator 16 is disposed in place of or in addition to the atmosphere opening passage 12b may be employed. An adequate gas which is necessary for the calibration process is filled in the calibration gas accommodator 16. When the predetermined conditions are satisfied, the controller 13 functioning as the calibration controller controls the valve device of the measurement/calibration switcher 12 so as to cause the calibration gas passage 12d to communicate with the measurement gas passage 12c. The calibration gas filled in the calibration gas accommodator 16 is introduced into the measurer 11 through the calibration gas passage 12d and the measurement gas passage 12c, and the gas sensors are calibrated based on the composition of the calibration gas.

Alternatively, a configuration where a cylinder in which a calibration gas of known concentration is filled is connected to the atmosphere opening passage 12b may be employed. In this case, the controller 13 functioning as the calibration controller controls the valve device so as to cause the atmosphere opening passage 12b to communicate with the measurement gas passage 12c. The calibration gas filled in the cylinder is introduced into the measurer 11 through the atmosphere opening passage 12b and the measurement gas passage 12c.

The biological information of the subject 20 which is to be measured by the measurer 11A of the monitoring apparatus 10A of the second embodiment is not limited to an ECG and the pulse wave. As required, the biological information may include information relating to the blood pressure, such as the pulse pressure, or a configuration where the cardiac output is obtained by using at least two of the kinds of information may be employed.

In the monitoring apparatus 10A of the second embodiment, a configuration may be employed where the function as the time measurer is realized by at least one of the calculator 11c and the measurement/calibration switcher 12A in place of or in addition to the controller 13.

The display 14 is not always necessary to be disposed as a part of the monitoring apparatus 10. A configuration where a displaying device which is disposed outside the monitoring apparatus 10, and which is communicably connected to the controller 13 functions as the display 14 may be employed.

The storage 15 is not always necessary to be disposed separately from the controller 13, and may be configured as a part of a memory of the processing circuit constituting the controller 13.

What is claimed is:

1. A biological information monitoring apparatus comprising:
   a measurer which is configured to measure a concentration of a predetermined gas contained in an expired gas of a subject;
   a display on which a measurement value of the concentration of the predetermined gas contained in the expired gas measured by the measurer is displayed;
   a calibration controller which, when a predetermined condition is satisfied, is configured to perform a calibration process on the measurer;
   a controller configured to function as a time measurer to acquire a remaining time before the calibration process is ended; and
   a display controller which is configured to cause an index indicating the remaining time to be displayed on the display,
   wherein, based on the predetermined condition, the time measurer selects one of a plurality of predetermined values which indicate times required for the calibration process, respectively, and, based on the selected one of the plurality of predetermined values, acquires the remaining time,
   wherein the remaining time is acquired after the calibration process has begun, and
   wherein, in the calibration process, the calibration controller is configured to cause at least one of an atmospheric gas and a calibration gas to be introduced into the measurer, the measurer being calibrated with at least one of the atmospheric gas and the calibration gas.

2. The biological information monitoring apparatus according to claim 1, wherein the index is at least one of a numeral and a progress bar.

3. A biological information monitoring apparatus comprising:
   a measurer which is configured to measure a concentration of a predetermined gas contained in an expired gas of a subject;
   a display on which a measurement value of the concentration of the predetermined gas contained in the expired gas measured by the measurer is displayed;
   a calibration controller which, when a predetermined condition is satisfied, is configured to perform a calibration process on the measurer;
   a controller configured to function as a time measurer to acquire a remaining time before the calibration process is ended; and
   a display controller which is configured to cause an index indicating the remaining time to be displayed on the display,
   wherein, based on information indicating a relationship between the predetermined condition and a time required for the calibration process, the time measurer calculates or acquires the remaining time, wherein the remaining time is acquired after the calibration process has begun, and wherein, in the calibration process, the calibration controller is configured to cause at least one of an atmospheric gas and a calibration gas to be introduced into the measurer, the measurer being calibrated with at least one of the atmospheric gas and the calibration gas.

4. The biological information monitoring apparatus according to claim 1, further comprising a calibration gas accommodator that accommodates the calibration gas.

5. The biological information monitoring apparatus according to claim 3, further comprising a calibration gas accommodator that accommodates the calibration gas.

* * * * *

UNITED STATES PATENT AND TRADEMARK OFFICE
CERTIFICATE OF CORRECTION

PATENT NO. : 10,058,286 B2
APPLICATION NO. : 13/862974
DATED : August 28, 2018
INVENTOR(S) : Shoichi Hosaka et al.

It is certified that error appears in the above-identified patent and that said Letters Patent is hereby corrected as shown below:

In the Specification

Column 2, Line 62, "information monitoring apparatus" should read --information monitoring apparatus 10--

Signed and Sealed this
Twentieth Day of November, 2018

Andrei Iancu
*Director of the United States Patent and Trademark Office*